US00PP14838P3

(12) United States Plant Patent
Fujinami

(10) Patent No.: US PP14,838 P3
(45) Date of Patent: Jun. 1, 2004

(54) *CARPINUS COREANA* PLANT NAMED 'KURO BIJIN'

(50) Latin Name: *Carpinus coreana*
Varietal Denomination: Kuro Bijin

(75) Inventor: Hikaru Fujinami, Kawaguchi (JP)

(73) Assignee: Hines Nurseries, Inc., Irvine, CA (US)

( * ) Notice: Subject to any disclaimer, the term of this patent is extended or adjusted under 35 U.S.C. 154(b) by 0 days.

(21) Appl. No.: 10/107,905

(22) Filed: Mar. 26, 2002

(65) Prior Publication Data

US 2003/0188356 P1 Oct. 2, 2003

(51) Int. Cl.[7] ..... A01H 5/00
(52) U.S. Cl. ..... Plt./226
(58) Field of Search ..... Plt./226

*Primary Examiner*—Kent Bell
*Assistant Examiner*—Louanne Krawczewicz Myers
(74) *Attorney, Agent, or Firm*—Christie, Parker & Hale, LLP

(57) ABSTRACT

A new plant variety of *Carpinus coreana* characterized by its chocolate brown leaf color throughout the growing season.

1 Drawing Sheet

Classification: *Carpinus coreana* Nak.
Variety denomination: 'Kuro Bijin'.

BACKGROUND OF THE INVENTION

The present invention relates to a new and distinct variety of *Carpinus coreana* Nak., which was discovered as a seedling selection in a cultivated planting of an unnamed, unpatented *Carpinus coreana* in Kawaguchi City, Saitama Prefecture, Japan by the originator, Mr. Hikaru Fujinami. The varietal denomination of the new variety is 'Kuro Bijin'.

The genus Carpinus is included in the family Betulaceae which comprises about 6 genera and over 100 species of deciduous, mostly monoecious trees and shrubs, native mostly to the Northern Hemisphere. Carpinus comprises approximately 35 species of deciduous, monoecious, medium or small sized trees originating in the Northern Hemisphere, many of which possess desirable ornamental characteristics.

*Carpinus coreana* possesses upright growth habit, with pendulous branches, broadly ovate leaves up to 5 cm long, with lustrous green foliage and veins in pairs, 10 to 12, hairy beneath, not impressed above. It generally possesses ornamental characteristics useful in the landscape.

SUMMARY OF THE INVENTION

The new variety was discovered as a seedling selection in a controlled planting of *Carpinus coreana* and differs from other cultivars known to the inventor in having chocolate brown leaf color throughout the growing season. Asexual reproduction of the new variety by grafting, performed in Kawaguchi City, Saitama Prefecture, Japan; Vacaville, Calif.; and Lewisberry, Pa. have confirmed that the distinctive characteristics of the new variety are stable and transmitted to succeeding generations, and the new variety reproduces true to type.

COMPARISON WITH PARENT

'Kuro Bijin' is distinguished from its parent and all other varieties of *Carpinus coreana* of which I am aware by its chocolate brown leaf color throughout the growing season.

BRIEF DESCRIPTION OF ILLUSTRATION

The accompanying illustrations show a plant of the new cultivar in a photographic illustration as true to color as is reasonably possible to make in an illustration of this character.

FIG. 1 illustrates the plant's unique foliage coloration.

DESCRIPTION OF THE NEW VARIETY

'Kuro Bijin' has not been observed under all possible environmental, cultural and light conditions. The following observations and descriptions are of plants grown in Vacaville, Calif., Lewisberry, Pa., and Saitama Prefecture, Japan. In this description, color references are to The Royal Horticultural Society Colour Chart (2001) and terminology used in the color descriptions herein refers to plate numbers in this color chart. Phenotypic expression may vary with light intensity, cultural, and environmental conditions.

Classification:
- *Botanical.*—*Carpinus coreana* Nak. 'Kuro Bijin'.
- *Parentage.*—Seedling selection from a controlled planting of *Carpinus coreana* (unnamed, unpatented).
- *Propagation.*—Grafting.

Plant:
- *Age of observed plant.*—The following description and color readings are of a 2-year-old plant grown in 5-gallon nursery containers in Vacaville, Calif. and Lewisberry, Pa.
- *Size.*—Typical 2-year-old Plant: About 90 cm to about 1.1 m tall; about 45 to about 55 cm wide. Observed Plant: Approximately 1 m tall, about 50 cm wide.
- *Habit.*—Upright plant with arching branches and pendulous branch tips.
- *Branching.*—Typical Number Branches: Approximately 100. Observed Number Branches: About 15. Size of Typical Plant Branch Length: About 25 cm to about 50 cm. Branch Diameter: About 1 cm at base. Observed Plant Branch Length: About 25 cm to about 50 cm. Branch Diameter: About 1 cm at base. Color: Near 200A. Lenticels: Near 199B. Color of New Shoots: Near 200A. Trunk Diamter: Approximately 1 cm in diameter at 10 cm above soil line. Bark Color: Near 200A.

Leaf:

*Shape.*—Broadly ovate.

*Base.*—Typical Plant: Obtuse to slightly oblique. Observed Plant: Obtuse to slightly oblique.

*Apex.*—Typical Plant: Acute to slightly acuminate. Observed Plant: Acute to slightly acuminate.

*Leaf size.*—Length: About 4 to about 5 cm. Width: About 3 cm. Arrangement: Alternate. Margin: Double serrate.

*Texture/substance.*—Lustrous throughout. Young Foliage Upper side: Near 186B. Underside: Near 186B. Mature Foliage Upper side: Near 92A. Underside: Near 92A. Venation Pattern Upper Surface: Veins in 10 to 12 pairs, not impressed. Under Surface: Fine hairs along mid-rib. Leaf Buds Color: Near 200B. Size: About 5 mm long. Shape: Conical; slender. Internodes: About 1.5 to 3.0 cm.

*Petioles.*—Length Typical Plant: About 8 mm to about 11 mm. Observed Plant: About 8 mm to about 11 mm. Diameter Typical Plant: Less than 1 mm. Observed Plant: Less than 1 mm. Color: Near 176B. Texture: Smooth.

*Stipules.*—Number per Petiole: About 2 at the base of each petiole. Length: About 3 mm. Width: About 1 mm. Apex: Long acuminate to subulate. Base: Sessile. Margin: Entire. Color: Near 199B.

*Hardiness.*—USDA Zone 7 (0° to 10° F.).

*Vigor.*—Moderate.

*Pests/diseases.*—None observed.

Inflorescence: None observed to date.

*Male and female catkins.*—None observed to date.

*Flowers.*—None observed to date.

*Bracts.*—None observed to date.

Reproductive organs: None observed to date.

*Pistils.*—None observed to date.

*Anthers.*—None observed to date.

*Stigma.*—None observed to date.

*Styles.*—None observed to date.

*Ovaries.*—None observed to date.

*Pollen.*—None observed to date.

*Fruit.*—None observed to date.

I claim:

1. A new and distinct variety of *Carpinus coreana* plant, named 'Kuro Bijin', substantially as shown and described.

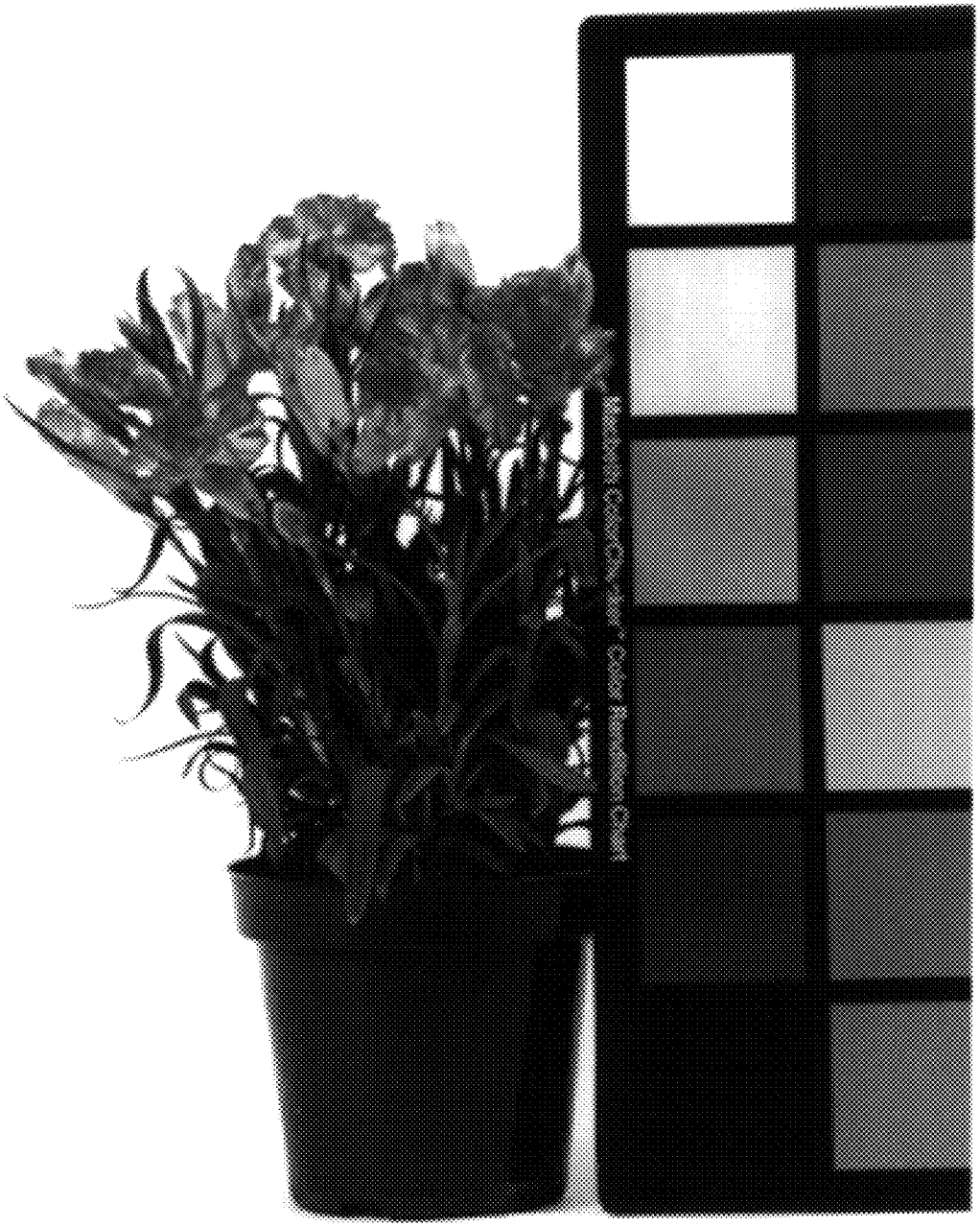

* * * * *